US005597304A

United States Patent [19]
Ray et al.

[11] Patent Number: 5,597,304
[45] Date of Patent: Jan. 28, 1997

[54] UNIVERSAL ALIGNMENT INDICATOR

[76] Inventors: Isaac Ray, 3700 Bedford Ave., Brooklyn, N.Y. 11229; Lawrence Avramenko, 3845 Lime Ave., Brooklyn, N.Y. 11224

[21] Appl. No.: 505,682

[22] Filed: Jul. 21, 1995

[51] Int. Cl.$^6$ .............. A61C 3/00; A61C 1/00; A61C 3/02
[52] U.S. Cl. .............. 433/75; 433/27; 433/76
[58] Field of Search .............. 433/27, 75, 76, 433/98, 215, 229, 72

[56] References Cited

U.S. PATENT DOCUMENTS

| | | | |
|---|---|---|---|
| 3,218,624 | 11/1965 | Zane | 433/27 |
| 3,462,842 | 8/1969 | Greenberg et al. | 433/27 |
| 3,508,334 | 4/1970 | Weissman | 32/67 |
| 3,839,797 | 10/1974 | Randolph | 433/27 |
| 4,306,866 | 12/1981 | Weissman | 433/215 |
| 4,824,367 | 4/1989 | Rosenstiel et al. | 433/75 |
| 5,055,042 | 10/1991 | Jansen | 433/76 |
| 5,133,660 | 7/1992 | Fenick | 433/76 |
| 5,456,013 | 10/1995 | Elias | 433/27 X |

Primary Examiner—Nicholas D. Lucchesi
Attorney, Agent, or Firm—Richard L. Miller, P.C.

[57] ABSTRACT

A device for alerting a dentist when the angular position of the drill and the angular position of the tooth being drilled do not correspond so that during drilling the angular position of the hole being drilled does not change. The device includes a drill transducer, a tooth transducer, a central control unit, and an alarm. The drill transducer is attachable to a dental drill and generates a drill angular position signal representing an angular position of the dental drill. The tooth transducer is removably attachable to a tooth and generates a tooth angular position signal representing an angular position of the tooth. The central control unit compares the drill angular position signal and the tooth angular position signal to each other to determine if the difference is within the value of a predetermined difference angular position. And, the alarm alerts when the drill angular position signal and the tooth angular position signal do not correspond with each other within the value of the predetermined difference angular position so that repositioning of the drill can be initiated.

14 Claims, 1 Drawing Sheet

UNIVERSAL ALIGNMENT INDICATOR

BACKGROUND OF THE INVENTION

The present invention relates to a dental drill alignment device. More particularly, the present invention relates to a dental drill alignment device that includes a first transducer attached to a dental drill for generating an angle signal, a second transducer affixed to a tooth for generating an angle signal, a central control unit for comparing the two angle signals to each other if they are within an acceptable predetermined difference tolerance value, and an alarm indicating when the angle signals do not correspond within the predetermined value.

Despite the sophistication of current dental technology, all dental operations are performed by hand and therefore their success depends totally on the experience and physical condition of the dentist.

Of extreme importance, is maintaining the dental drill in the desired angular position during the dental operation. This, however, can present a problem since both the dental drill and the patient are not stable in space and their orientation can be frequently changed during the dental operation. This will cause the drilling direction to change and present a serious deficit when specifically oriented holes must be drilled in a tooth.

During many dental operations it is often necessary to drill these specifically orientated holes in a tooth. For example, in order to provide an artificial crown for a tooth, the crown portion of the tooth is first ground down to the root surface. Thereafter a peg or support, usually gold, for the artificial crown, is inserted into the root by means of specifically orientated holes drilled into the root.

Numerous innovations for dental drill orientating devices have been provided in the prior art that will be described. However, even though these innovations may be suitable for the specific individual purposes to which they address, they differ from the present invention in that they do not teach a dental drill alignment device that includes a first transducer attached to a dental drill for generating an angle signal, a second transducer affixed to a tooth for generating an angle signal, a central control unit for comparing the two angle signals to each other to be within a predetermined difference tolerance value, and an alarm for indicating when the two angle signals do not correspond within the predetermined difference tolerance value.

For example, U.S. Pat. No. 3,508,334 to Weissman teaches a dental paralleling guide adapted to be pivotally and vertically held in a desired part of a tooth so as to provide for the drilling of parallel holes in the tooth.

Another example, U.S. Pat. No. 4,306,866 to Weissman teaches an adjustable drill guide that includes an elongated hollow member with an elongated bar that is telescopically received in the hollow member. A locking device secures the bar within the hollow member at a preselected extended position. A locating pin depends from the distal end of the bar and is received in a hole provided in a first tooth while the body member is disposed in a channel extending from the first tooth to at least one adjacent tooth. A drill bushing passes through the distal end of the hollow member and extends upwardly therefrom for guiding a drill during the formation of a hole in an adjacent tooth.

Still another example, U.S. Pat. No. 4,824,367 to Rosenstiel teaches a dental drill alignment indicator that allows the initial position of the axis of a cutter to be related by means of electronic "spirit levels" to a selected axis. Deviation from this axis by more than a predetermined amount is indicated by light sources. By means of a code these light sources indicate how the dentist must move the cutter to return to the correct axis.

Finally, another example, U.S. Pat. No. 5,055,042 to Jansen teaches a dental drill that includes a drill head carrying a drill bit and a telescopic drilling template attached to the drill head. After a first hole has been drilled in the tooth with the drill bit, the template is inserted into that hole.

It is apparent that numerous innovations for dental drill orientating devices have been provided in the prior art that are adapted to be used. Furthermore, even though these innovations may be suitable for the specific individual purposes to which they address, they would not be suitable for the purposes of the present invention as heretofore described.

SUMMARY OF THE INVENTION

Accordingly, an object of the present invention is to provide a universal alignment indicator that avoids the disadvantages of the prior art.

Another object of the present invention is to provide a universal alignment indicator that is simple and inexpensive to manufacture.

Still another object of the present invention is to provide a universal alignment indicator that is simple and easy to use.

Yet still another object of the present invention is to provide a universal alignment indicator that alerts a dentist when the angular position of the drill and the angular position of the tooth being drilled do not correspond closely enough to each other within a predetermined difference tolerance value during the drilling of a hole.

Still another object of the present invention is to provide a universal alignment indicator that includes drill apparatus, tooth apparatus, comparing apparatus, and alarm apparatus.

Yet still another object of the present invention is to provide a universal alignment indicator wherein the drill apparatus is attachable to a dental drill and generates a drill angular position signal representing an angular position of the dental drill.

Still another object of the present invention is to provide a universal alignment indicator wherein the tooth apparatus is removably attachable to a tooth and generates a tooth angular position signal representing an angular position of the tooth.

Yet still another object of the present invention is to provide a universal alignment indicator wherein the comparing apparatus compares the drill angular position signal and the tooth angular position signal to each other to determine if the difference is within an acceptable predetermined difference angular value.

Still another object of the present invention is to provide a universal alignment indicator wherein the alarm apparatus alerts when the drill angular position signal and the tooth angular position signal do not correspond to each other within the value of the predetermined tolerance difference angular position so that repositioning of the drill can be initiated.

Yet still another object of the present invention is to provide a universal alignment indicator wherein the drill apparatus is a gravity sensing drill transducer.

Still another object of the present invention is to provide a universal alignment indicator wherein the drill angular position signal has a drill signal "X"-component and a drill signal "Y"-component.

Yet still another object of the present invention is to provide a universal alignment indicator that further includes drill attaching apparatus for attaching the gravity sensing drill transducer to the drill.

Still another object of the present invention is to provide a universal alignment indicator wherein the drill attaching apparatus is a clamp.

Yet still another object of the present invention is to provide a universal alignment indicator wherein the tooth apparatus is a gravity sensing tooth transducer.

Still another object of the present invention is to provide a universal alignment indicator wherein the tooth angular position signal has a tooth signal "X"-component and a tooth signal "Y"-component.

Yet still another object of the present invention is to provide a universal alignment indicator that further includes tooth attaching apparatus for attaching the gravity sensing tooth transducer to the tooth.

Still another object of the present invention is to provide a universal alignment indicator wherein the tooth attaching apparatus is a clamp.

Yet still another object of the present invention is to provide a universal alignment indicator wherein the comparing apparatus is a central control unit.

Still another object of the present invention is to provide a universal alignment indicator wherein the alarm apparatus is senses selected from a group consisting of audible and visual.

Yet still another object of the present invention is to provide a universal alignment indicator wherein the audible and the visual are produced by the central control unit.

Finally, another object of the present invention is to provide a method for using a precise orientating tooth drilling device that includes the steps of generating a drill angular positioning signal representing an angular position of a drill, generating a tooth angular positioning signal representing an angular position of a tooth, comparing the drill angular positioning signal and the tooth angular positioning signal to a value of a predetermined angular position difference tolerance, and alerting when the drill angular positioning signal and the tooth angular positioning signal do not correspond to each other within the value of the predetermined difference tolerance angular position.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures on the drawing are briefly described as follows.

LIST OF REFERENCE NUMERALS UTILIZED IN THE DRAWING

10—universal alignment indicator of the present invention
12—tooth portion
14—tooth
15—"X"-coordinate
16—patient
17—"Y"-coordinate
18—drill portion
20—dental drill
21—drill bit longitudinal axis
22—dentist
23—drill bit
24—tooth clamp
26—gravity sensing tooth transducer
28—tooth output signal
30—tooth signal "X"-component
32—tooth signal "Y"-component
36—drill clamp
38—gravity sensing drill transducer
40—drill output signal
42—drill signal "X"-component
44—drill signal "Y"-component
46—central control unit
48—desired tooth hole orientation line
49—hole that is to be drilled in the tooth
50—tolerance value set control
52—alarm signal
54—alarm
56—desired angular difference value input

DETAILED DESCRIPTION OF THE PREFERRED EMBODIMENT

Figure 1:
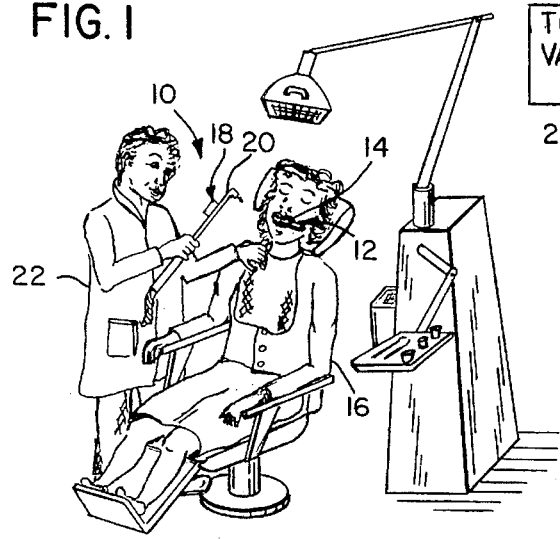
FIG. 1 is a diagrammatic perspective view illustrating a typical embodiment of the instant invention in use.

Referring now to the figures in which like numerals indicate like parts, and particularly to FIG. 1, the universal alignment indicator of the present invention is shown generally at 10 having a tooth portion 12 attached to a tooth 14 of a patient 16 and a drill portion 18 attached to a dental drill 20 being held by a dentist 22.

Figure 3:
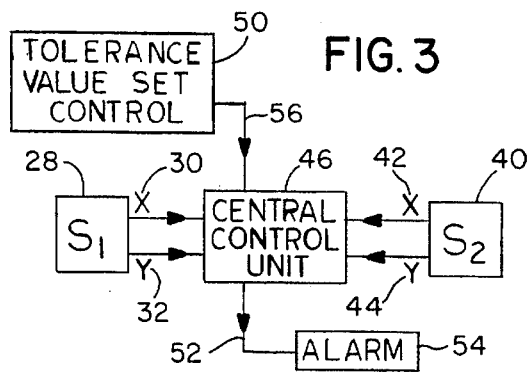
FIG. 3 is a block diagram thereof.
Figure 2:
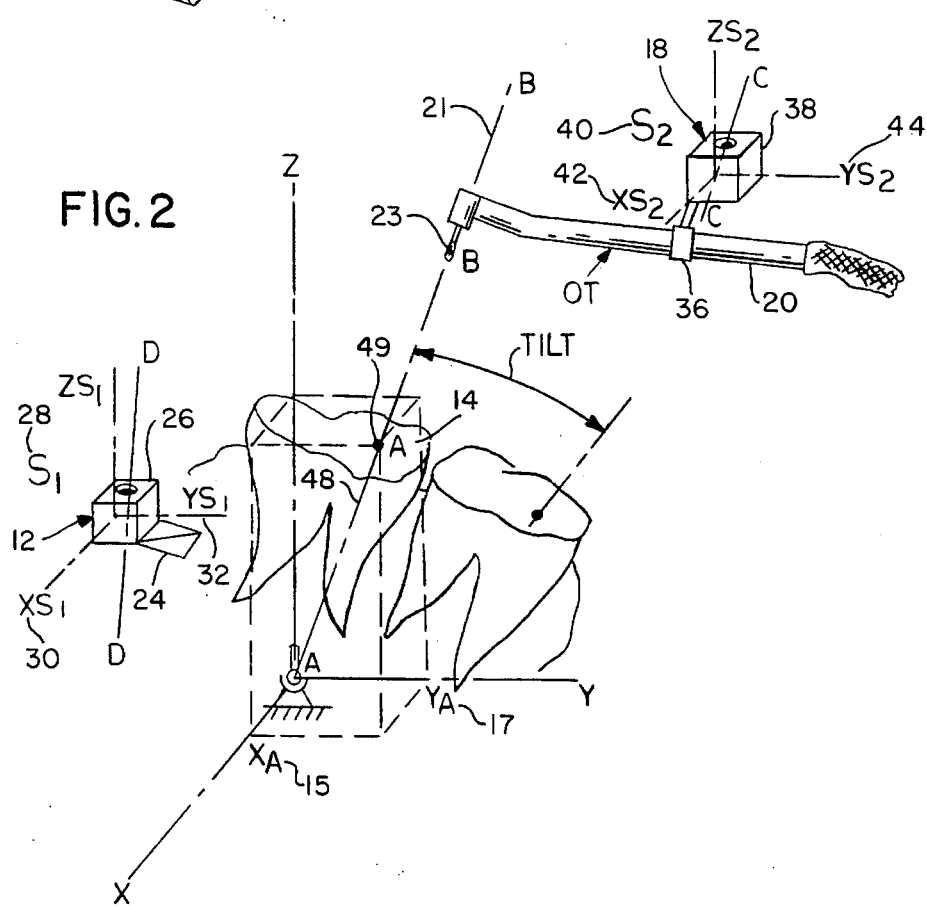
FIG. 2 is a diagrammatic view illustrating how some of the components of the instant invention cooperate with each other.

The configuration of the universal alignment indicator 10 can best be seen in FIGS. 2 and 3, and as such, will be discussed with reference thereto.

The tooth portion 12 includes a tooth clamp 24 for removably mounting a gravity sensing tooth transducer 26 to the tooth 14 of the patient 16. The gravity sensing tooth transducer 26 senses its orientation, relative to vertical, and produces a tooth output signal 28 that has a tooth signal "X"-component 30 and a tooth signal "Y"-component 32.

The drill portion 18 includes a drill clamp 36 for mounting a gravity sensing drill transducer 38 to the drill 20. The gravity sensing drill transducer 38 senses its orientation, relative to vertical, and produces a drill output signal 40 that has a drill signal "X"-component 42 and a drill signal "Y"-component 44.

In operation, the tooth portion 12 is turned on and attached to the tooth 14. The gravity sensing tooth transducer 26 senses the orientation of the tooth 14, relative to its "X"-coordinate 15 and its "Y"-coordinate 17, and produces the tooth signal "X"-component 30 and the tooth signal "Y"-component 32. The tooth signal "X"-component 30 and the tooth signal "Y"-component 32 are digital or analog representations of the random tilt of the tooth 14 which are fed to a central control unit 46 where they are memorized.

Next, the drill portion 18 is turned on. The gravity sensing drill transducer 38 senses the orientation of the drill 20 and produces the drill signal "X"-component 42 and the drill signal "Y"-component 44 which are digital or analog representations of the random tilt of the drill 20. These components are fed to the central control unit 46 where they are memorized.

A desired tooth hole orientation line 48 for a hole 49 that is to be drilled in the tooth 14 is arrived at by angular positioning the drill bit longitudinal axis 21 of the drill bit 23 collinear with the desired tooth hole orientation line 48 for the hole 49. The central control unit 46 is then programmed with the "X" and "Y" coordinates of the desired difference angular orientation of the desired tooth hole orientation line 48 and a desired tolerance is set with tolerance value set control 50.

As the drilling proceeds, the central control unit 46 constantly compares the tooth signal "X"-component 30, the tooth signal "Y"-component 32, the drill signal "X"-component 42, and the drill signal "Y"-component 44 to determine that they are within acceptable value set of each other.

If, however, when either the tooth signal "X"-component 30, the tooth signal "Y"-component 32, the drill signal "X"-component 42, and the drill signal "Y"-component 44 do not correspond respectively within desired predetermined difference value set with the tolerance value set control 50, indicating that the dentist 22 and/or the patient 16 have moved relative to each so that the drill bit longitudinal axis 21 is no longer parallel with the desired tooth hole orientation line 48, an unbalance is present and an alarm signal 52 is generated activating an alarm 54.

The alarm 54 will continue until the tooth signal "X"-component, the tooth signal "Y"-component 32, the drill signal "X"-component 42, and the drill signal "Y"-component 44 do correspond within the predetermined desired angular difference value input 56 by tolerance value set control 50, indicating that the dentist 22 and/or the patient 16 have moved relative to each so that the drill bit longitudinal axis 21 is now parallel with the desired tooth hole orientation line 48, and a balance is present.

The alarm 54 can be audible and/or visual and may be a part of the central control unit 46 utilizing the monitor for the visual alarm and a sound card for the audible alarm, but is not limited to that.

Depending upon the accuracy required during the operation on the tooth 14, a window of a predetermined amount can be provided in the central control unit 46. This window will prevent the alarm signal 40 from being generated even when the tooth signal "X"-component, the tooth signal "Y"-component 32, the drill signal "X"-component 42, and the drill signal "Y"-component 44 do not correspond within the predetermined desired angular difference tolerance value.

Furthermore, since any desired tooth hole orientation line 48 for the hole 49 can be readily maintained, multiple parallel holes 49 can also be achieved without the need for additional apparatus, such as templates or the like, to be placed in the mouth of the patient 16.

It will be understood that each of the elements described above, or two or more together, may also find a useful application in other types of constructions differing from the types described above.

While the invention has been illustrated and described as embodied in a universal alignment indicator, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A precise orientating tooth drilling device, comprising:
   a) drill orientation means attachable to a dental drill for generating a drill angular position signal representing an angular position of said dental drill;
   b) tooth orientation means removably attachable to a tooth for generating a tooth angular position signal representing an angular position of said tooth;
   c) comparing means for comparing said drill angular position signal and said tooth angular position signal to each other and determining if a difference therebetween is within a predetermined value; and
   d) alarm means for alerting when said difference between said drill angular position signal and said tooth angular position signal is not within said predetermined value, so that repositioning of said drill can be initiated.

2. The device as defined in claim 1, wherein said drill orientation means includes a gravity sensing drill transducer.

3. The device as defined in claim 2, wherein said drill angular position signal has a drill signal "X"-component and a drill signal "Y"-component.

4. The device as defined in claim 3; further comprising drill attaching means for attaching said gravity sensing drill transducer to said drill.

5. The device as defined in claim 4, wherein said drill attaching means includes a clamp.

6. The device as defined in claim 1, wherein said tooth orientation means includes a gravity sensing tooth transducer.

7. The device as defined in claim 6, wherein said tooth angular position signal has a tooth signal "X"-component and a tooth signal "Y"-component.

8. The device as defined in claim 7; further comprising tooth attaching means for attaching said gravity sensing tooth transducer to said tooth.

9. The device as defined in claim 8, wherein said tooth attaching means includes a clamp.

10. The device as defined in claim 1, wherein said comparing means includes a central control unit.

11. The device as defined in claim 10, wherein said alarm means includes signals selected from a group consisting of audible and visual.

12. The device as defined in claim 11, wherein said audible and said visual signals are produced by said central control unit.

13. A method for using a precise orientating tooth drilling device, comprising the steps of:
   a) generating a drill angular positioning signal representing an angular position of a dentist drill;
   b) generating a tooth angular positioning signal representing an angular position of a tooth of a patient;
   c) comparing said drill angular positioning signal and said tooth angular positioning signal to each other and determining if a difference therebetween is within a predetermined value; and
   d) alerting when said difference between said drill angular positioning signal and said tooth angular positioning signal is not within said predetermined value.

14. A precise orientating tooth drilling device, comprising:
   a) means for generating a drill angular positioning signal representing an angular position of a dentist drill;
   b) means for generating a tooth angular positioning signal representing an angular position of a tooth of a patient;
   c) means for comparing said drill angular positioning signal and said tooth angular positioning signal to each other and determining if a difference therebetween is within a predetermined value; and d) means for alerting when said difference between said drill angular positioning signal and said tooth angular positioning signal is not within said predetermined value.

* * * * *